United States Patent [19]

Sundheimer

[11] Patent Number: 4,617,065
[45] Date of Patent: Oct. 14, 1986

[54] METHOD FOR LIQUID DISINFECTING AND STERILE RINSING

[75] Inventor: Craig S. Sundheimer, Salt Lake City, Utah

[73] Assignee: American Sterilizer Company, Erie, Pa.

[21] Appl. No.: 820,346

[22] Filed: Jan. 21, 1986

Related U.S. Application Data

[62] Division of Ser. No. 683,814, Dec. 20, 1984.

[51] Int. Cl.$^4$ .............................................. B08B 3/04
[52] U.S. Cl. .................................... 134/25.4; 134/26; 422/28
[58] Field of Search .................. 134/25.4, 91, 92, 95, 134/98, 101, 100, 103, 111, 115 R, 147, 148, 151, 154, 155, 166 R, 169 R, 170, 186, 187, 188, 200, 26; 422/292, 300, 7; 68/133, 181 R, 181 D, 208

[56] References Cited

U.S. PATENT DOCUMENTS

| | | | |
|---|---|---|---|
| 484,927 | 10/1892 | Boeckmann | 422/292 |
| 553,561 | 1/1896 | Lundholm | 422/300 |
| 1,433,216 | 10/1922 | McCutchen | 134/147 X |
| 1,473,209 | 11/1923 | Cook | 68/181 R |
| 2,314,673 | 3/1943 | Walker | 134/200 X |
| 2,676,088 | 4/1954 | Bilde et al. | 68/181 R X |

FOREIGN PATENT DOCUMENTS

38483 12/1923 Norway ............................. 134/187

*Primary Examiner*—Philip R. Coe
*Attorney, Agent, or Firm*—Robert D. Yeager; Christine R. Ethridge

[57] ABSTRACT

A method for disinfecting articles placed within an apparatus for use with a conventional supply of fluid. The apparatus includes an outer vessel, an inner vessel so disposed within the outer vessel that an outer chamber is defined therebetween, means for covering the inner vessel, means of introducing fluid into the inner vessel, and means for selectively draining the inner and outer vessels. There may also be means for agitating the fluid in the inner vessel. The method includes the step of washing the articles, rinsing with fluid, so applying disinfectant to the articles that the disinfectant fills the inner vessel and flows through an interface between the inner vessel and a cover on the inner vessel to so fill the outer chamber that the inner vessel is submerged, draining the inner and outer vessel, spraying sterile fluid onto the articles, so filling the inner vessel with the sterile fluid that the articles are submerged and the sterile fluid overflows through the interface and over the exterior surface of the cover to establish a direction of flow which prevents the entrance of contaminants into the inner vessel, but does not fill the outer chamber so that the exterior of the inner vessel is not submerged. The sterile fluid flows over the exterior of the inner vessel. The sterile fluid is agitated in the inner vessel, then drained from the inner and outer vessels.

5 Claims, 6 Drawing Figures

METHOD FOR LIQUID DISINFECTING AND STERILE RINSING

This is a divisional of co-pending application Ser. No. 683,814 filed on Dec. 20, 1984.

BACKGROUND OF THE INVENTION

1. Field of the Invention

The present invention relates to methods for disinfecting articles, and, more particularly, to a method of disinfecting both the articles and an inner vessel.

2. Description of the Prior Art

There are currently no automated systems available for consistently providing completely disinfected medical instruments after rinsing. The conventional automated systems are often adequate for disinfecting the instruments during the initial wash or disinfect cycle but fail to maintain the instruments in a disinfected state following the rinsing cycle.

U.S. Pat. No. 3,893,843 discloses an automated system for disinfecting inhalation therapy and anesthesia items which cannot be subjected to high heat. Contamination by waterborne microorganisms during and following the rinsing cycle was evidently not a concern and is not addressed.

Waterborne microorganisms are of great concern as a source of contamination during the processing of instruments. Droplets of liquid from surfaces on those portions of the system which are not part of the disinfected field (have not been in continuous contact with a disinfectant) can fall on the disinfected instruments when lids are opened or when trays are jostled and the instruments removed, thereby contaminating the instruments. Of prime concern for purposes of the present invention is the potential for such droplets to contaminate disinfected instruments. Airborne microorganisms which present problems after processing, during drying and storing are not addressed in the present invention.

Manual methods of disinfecting medical instruments involve rinsing the instruments, washing in soapy water in a basin, soaking with 2% gluteraldehyde or a similar disinfectant, and rinsing with sterile water. A thorough rinse with sterile water for typical medical instruments such as endoscopes, may require approximately two liters of presterilized water. The manual method may yield completely disinfected instruments with greater consistency than the conventional automated methods but requires more counterspace and ancillary instruments, and is more labor intensive.

Osuch U.S. Pat. No. 2,246,104, which issued on June 17, 1941; Sacks et al. U.S. Pat. No. 2,743,733, which issued on May 1, 1956; Wanzer U.S. Pat. No. 2,788,008, which issued on April 9, 1957; and Faust et al. U.S. Pat. No. 3,590,683, which issued on July 6, 1971 disclose the use of various apparatus, each of which includes an inner vessel disposed within an outer vessel. The apparatuses and methods provided by those patents do not provide a means or method for consistently yielding completely disinfected instruments from an automated system following the rinsing cycle. The potential for droplet contamination is not addressed.

Accordingly, there is a need for a method for disinfecting medical instruments which will maintain the instruments in a disinfected state during and following the rinsing cycle. There is a further need for a method of disinfecting medical instruments which will eliminate the possibility of contaminated droplets entering the disinfected field following the disinfection of the instruments.

SUMMARY OF THE INVENTION

The present invention utilizes a system as disclosed in copending application Ser. No. 683,814, for providing disinfected articles adapted for use with a conventional supply of fluid. The system includes apparatus which includes an outer vessel having a lid, an inner vessel adapted for receiving the articles, the inner vessel being so disposed within the outer vessel that an outer chamber is defined therebetween, means, preferably a plurality of spray nozzles, for introducing fluid into the inner vessel, means for so covering the inner vessel that an interface is defined between the inner vessel and the covering means, and means for selectively draining the inner vessel and the outer chamber. The covering means is preferably adapted to permit fluid which fills the inner vessel to overflow through the interface to establish a direction of flow from the inner vessel over the exterior of the covering means and into the outer chamber, the direction of flow providing a barrier against the entrance of contaminants through the interface into the inner vessel. The outer chamber is so associated with the inner vessel that at least the interface and the covering means are submerged by the fluid flowing into the outer chamber. Preferably, the inner vessel is completely submerged by the fluid. The inner vessel and the covering means may be adapted for removal from the outer vessel. The apparatus may include means for agitating the fluid in the inner vessel.

The system also includes means, perferably a washer-first disinfectant solution holding container and an injector adapted for connection to the supply of fluid, for selectively introducing the solution into the supply of fluid for mixture with the fluid prior to introduction into the inner vessel, means for selectively sterilizing the fluid, preferably a plurality of filters adapted for removing microbes from the fluid prior to introduction into the inner vessel and a plurality of first valve means for controlling each of the selective introduction means and the selective sterilizing means. The system may also include means for selectively recycling a second disinfectant for introduction and reintroduction into the inner vessel and a plurality of second valve means for controlling the recycling means. The recycling means preferably includes a pump, a reservoir for the disinfectant and a plurality of conduits each having one of the second valves for so channeling the second disinfectant between the inner vessel and the reservoir that dilution is minimized.

The present invention provides a method for disinfecting articles and the exterior and interior surfaces of the vessel in which the articles are disposed. The method is for use in an apparatus which is adapted for use with a conventional supply of fluid and which has an outer vessel and an inner vessel so disposed within the outer vessel that an outer chamber is defined therebetween. The method includes the steps of placing the articles in the inner vessel, washing the articles, draining the inner vessel, and so applying a disinfectant to the articles that the disinfectant fills the inner vessel and flows through an interface between the inner vessel and a cover on the inner vessel to so fill the outer chamber that the inner vessel is submerged for a period of time sufficient to disinfect the articles and the inner vessel. The method also includes the further steps of draining the inner vessel and the outer chamber, spraying sterile fluid onto the articles, so filling the inner vessel with sterile fluid that the articles are submerged and the fluid flows through the interface and over the exterior of the cover, establishing a direction of flow for preventing the entrance of contaminants into the inner vessel, and rinsing the exterior of the cover, for a period of time sufficient to soak the articles, agitating the sterile fluid within the inner vessel, and draining the inner vessel and the outer chamber.

The inner vessel is preferably filled by closing a drain in the inner vessel before fluid is introduced into the inner vessel. The outer chamber is preferably filled by closing a drain in the outer vessel and the drain in the inner vessel. The inner vessel and the outer chamber are preferably drained by opening the drains in the respective vessels.

BRIEF DESCRIPTION OF THE DRAWINGS

The following detailed description of the preferred embodiment can better be understood if reference is made to the drawings in which.

DETAILED DESCRIPTION OF THE PREFERRED EMBODIMENT

FIGS. 1 through 6 illustrate the preferred embodiment of the system 10 and the apparatus 20 used to practice the method of the present invention.

Figure 6:
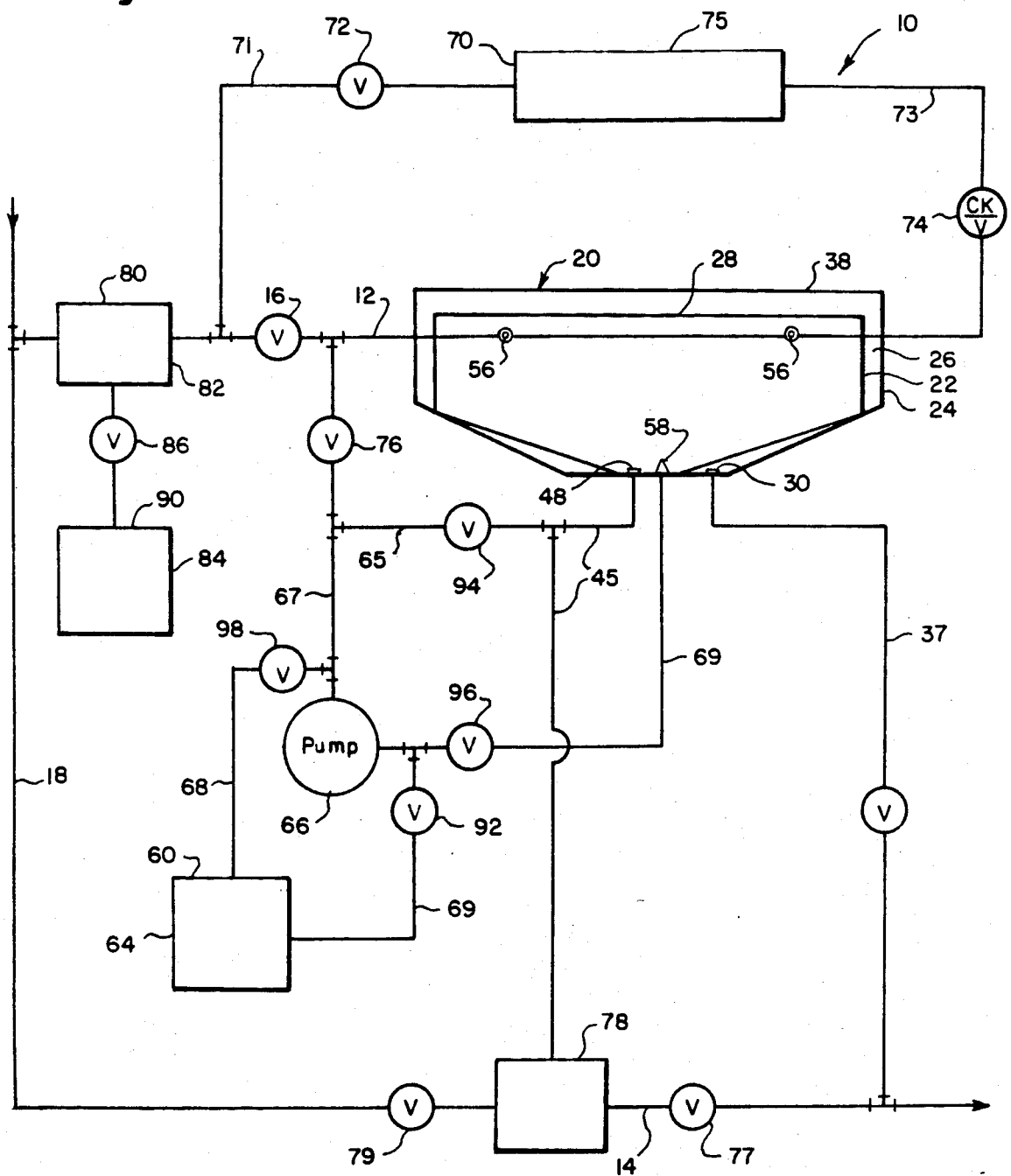
FIG. 6 is a schematic view of the system of the invention.

Referring to FIG. 6, the system 10, which can be used with a conventional fluid supply, includes apparatus 20, a means 80 for selectively introducing a washer-disinfectant solution into the fluid supply, a means 70 for selectively sterilizing the fluid, and a means 60 for selectively recycling a second disinfectant for reintroduction into the apparatus. The system may also include a means 90 for selectively introducing a second washer solution into the apparatus.

Figure 1:
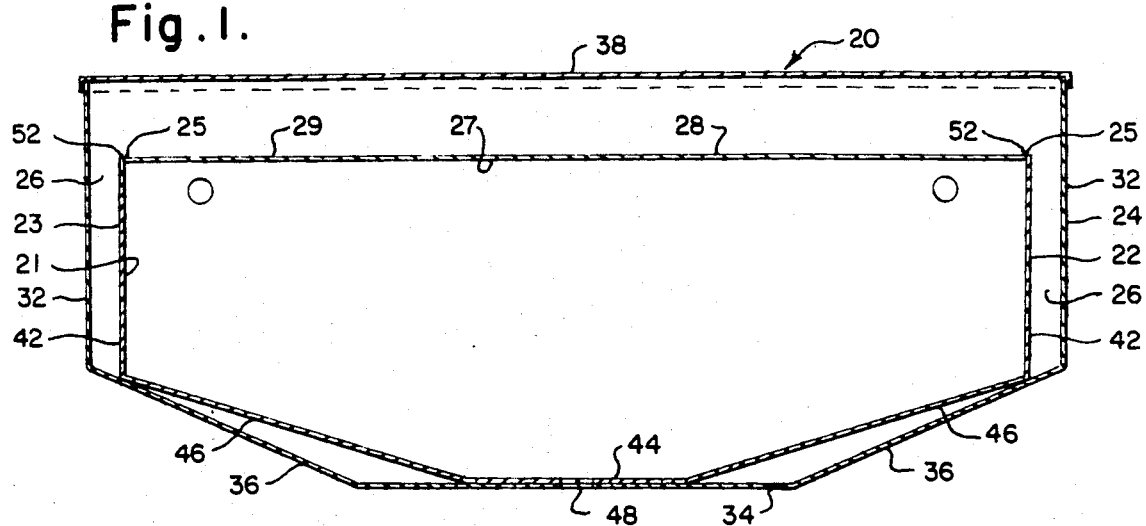
FIG. 1 is a longitudinal section view of the preferred embodiment of the apparatus used to practice the method of the invention.
Figure 2:
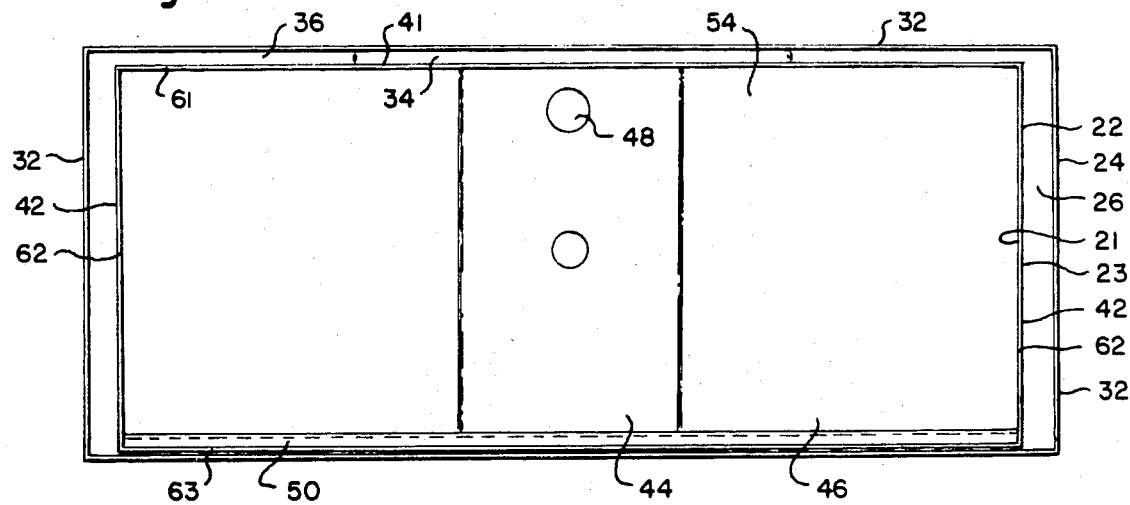
FIG. 2 is a top view of the apparatus of FIG. 1 with the lid and cover removed.
Figure 3:
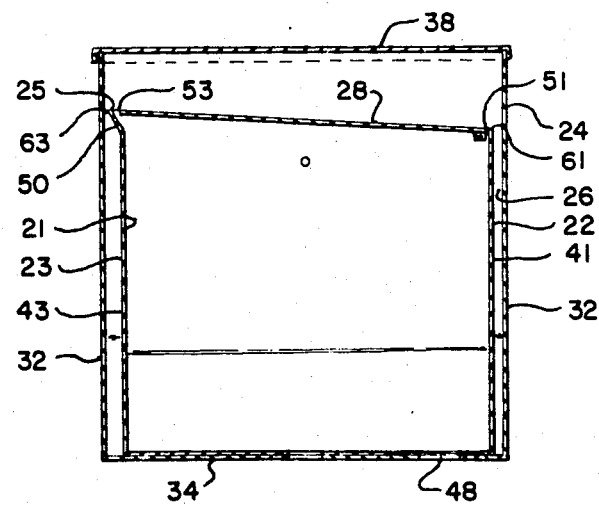
FIG. 3 is a transverse section view of the apparatus of FIG. 1.

Referring to FIGS. 1, 2 and 3, the apparatus 20, which is preferably a washer-disinfector/sterilizer, includes inner vessel 22 with cover 28 and outer vessel 24 with lid 38. A chamber 26 is defined between the two vessels 22 and 24.

Figure 4:
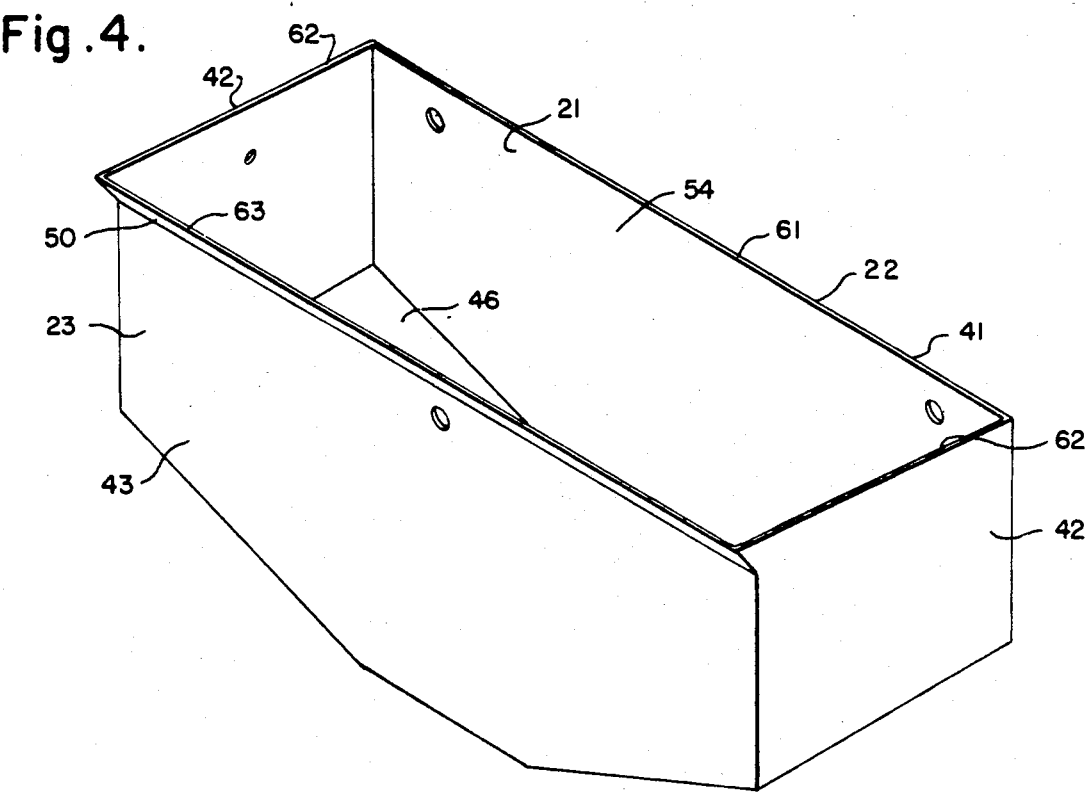
FIG. 4 is an isometric view of the inner vessel without the cover.
Figure 5:
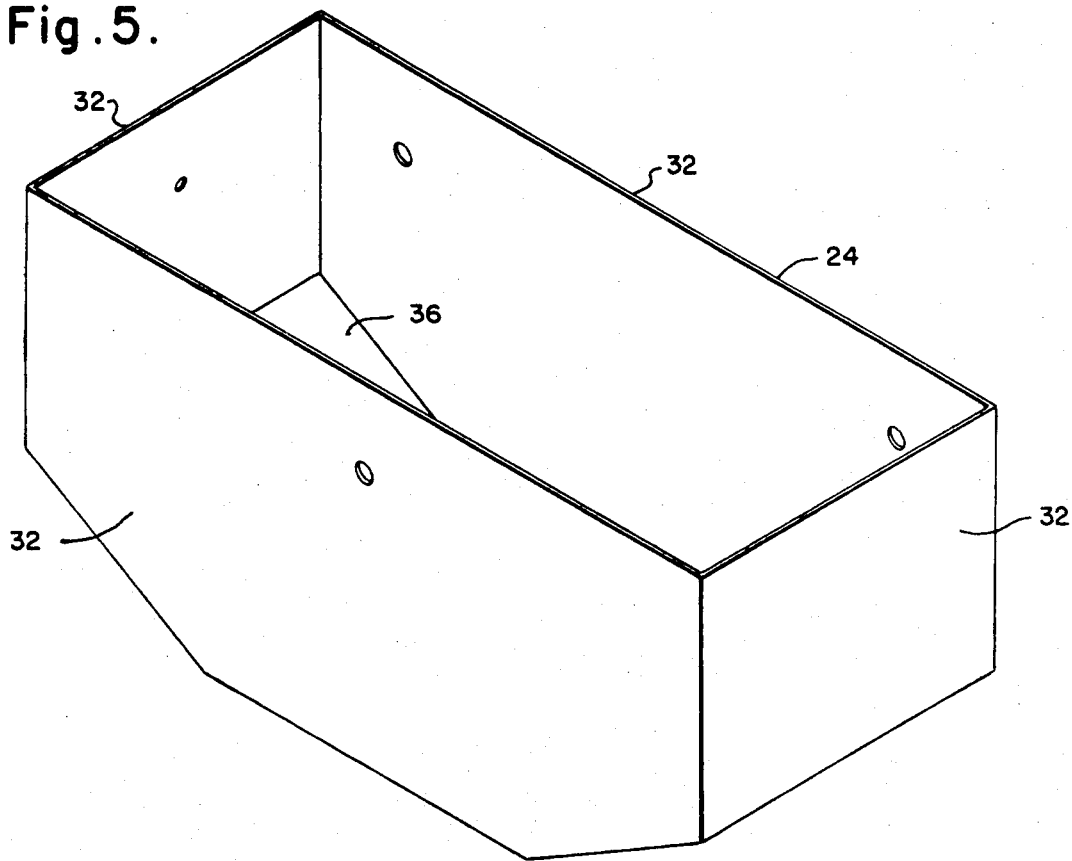
FIG. 5 is an isometric view of the outer vessel without the lid.

Referring to FIG. 4, inner vessel 22 has interior surface 21, exterior surface 23, back wall 41 with rim 61, front wall 43 with lip 50 and rim 63, two side walls 42, each with a rim 62, bottom wall 44 and two sloping bottom walls 46, each of which joins one of the side walls 42 to an opposite end of the bottom wall 44. Lip 50 extends outwardly from inner vessel 22 and upwardly from front wall 43. Rims 61, 62, and 63 define the periphery of an opening 54. Rims 62 rise from rim 61 to meet rim 63 of the upwardly and outwardly extending lip 50. Inner vessel 22 receives the articles to be disinfected.

Cover 28 has a front edge 53, two side edges 52 and a back edge 51 which is attached by any suitable known means, such as hinges, to rim 61 of back wall 41. Cover 28 fits into and over opening 54 so that front edge 53 rests against the interior surface 21 of lip 50. Cover 28 slopes downwardly from front edge 53 to back edge 51 in substantial alignment with the rise of rims 62 from rim 61 to rim 63. An interface 25 is defined where rims 61, 62, and 63 engage cover edges 51, 52, and 53.

Outer vessel 24 has four sides 32, a bottom 34 and two sloping bottom sections 36, each of which extends from one side 32 to an opposite edge of the bottom 34. Outer vessel 24 also has a drain 30 which can be selectively operated simultaneously with, or independently of, drain 48 in inner vessel 22.

Fluid from fluid supply line 12 is introduced into inner vessel 22 by spray nozzles 56. Additional means of introducing fluid into inner vessel 22 can be used. For example, agitator 58 may selectively deliver fluid to inner vessel 22 while performing the agitation function. Other kinds of known, specialized piping arrangements (not shown) can also be used to introduce a fluid into the inner vessel 22. Baskets adapted for holding specialized articles (not shown) may be coupled to the additional piping.

The means 80 for selectively introducing a washer-disinfectant solution into the fluid supply includes a container 84 for holding a solution of washing detergent and a disinfectant, such as any commercially available single-use iodophor, an injector 82 for metering the solution, or iodophor, into the fluid supply line 12 and a valve 86 for selectively controlling the introduction of the solution into the injector 82. The valve 86 may be a solenoid valve or any suitable known valve.

The fluid supply line 12 channels the detergent-disinfectant-fluid mixture into the inner vessel 22 through the spray nozzles 56 or through any additional or alternative suitable known means for introducing fluid into the inner vessel 22. A valve 16, preferably another solenoid valve, selectively controls the introduction of fluid or the detergent-disinfectant-fluid mixture into inner vessel 22. The fluid supply line 12 passes through outer vessel 24, into inner vessel 22. Any suitable known means for effectively sealing the areas through which the supply line 12 passes may be employed.

The means 70 for selectively sterilizing the fluid prior to introduction into the inner vessel 22 includes a series of filters 75, two conduits 71 and 73, and two valves 72 and 74. The filters 75 can be any commercially available filters which remove medically undesirable microbes from the fluid as it passes through the series of filters 75.

Conduit 73 connects filters 75 to the inner vessel 22 by passing through outer vessel 24 to spray nozzles 56. Suitable sealing means should be employed to prevent leakage in the areas through which conduit 73 passes. Valve 72 is preferably a solenoid valve and is disposed along conduit 71 for selectively controlling the introduction of fluid into the filters 75. Valve 74 is preferably a check valve and is disposed along conduit 73 for selectively controlling the introduction of the sterilized fluid into inner vessel 22. The valves 72 and 74 can be selectively manipulated to pass disinfectant into the filters 75 to soak the filters 75. In this way, microbes in the filters 75 are killed and the useful life of the filters 75 can be increased.

The means 60 for selectively recyleing a second disinfectant for reintroduction into the inner vessel 22 includes a reservoir 64 for holding a concentrated disinfectant, a pump 66 and a series of conduits and valves for selectively channeling the disinfectant from the inner vessel 22 to the reservoir 64, and from the reservoir 64 through the pump 66 back into the inner vessel 22 for reuse. The arrangement of the conduits and valves can be any suitable arrangement that minimizes the dead space and any dilution with the fluid to insure the maintenance of efficient concentrations of the second disinfectant.

Referring to FIG. 6, one possible arrangement is shown which includes conduit 67 which connects the pump 66 to fluid supply line 12 at a point between valve 16 and outer vessel 24, conduit 68 which connects reservoir 64 to pump 66, conduit 69 which connects the inner vessel 22 to the reservoir 64, valve 76 on conduit 67 for selectively controlling the introduction of the second disinfectant through the spray nozzles 56, and valves 92, 96, and 98 on conduits 69 and 68, respectively, for selectively controlling the paths for introduction of the second disinfectant from the reservoir 64 to the pump 66.

Conduit 45 connects drain 48 in inner vessel 22 to conduit 65 having valve 94 for selectively channeling the second-disinfectant from the inner vessel 22 to the reservoir 64. When valve 94 is closed, conduit 45 can channel fluid to a drain line 14.

A conduit 18 may channel fluid from supply line 12 to conduit 45 for delivery into the inner vessel 22 or diversion to conduit 65. The function of the direct connection to the fluid supply line 12 is to flush the conduits and provide alternative paths of fluid introduction. It should be appreciated that a wide variety of suitable conduit arrangements can be employed without exceeding the scope of the claimed invention.

An injector 78 and valves 79, preferably a solenoid valve, may be placed at the juncture of conduits 18, 45, and 14 in order to appropriately direct the fluid. Another valve 77, also preferably a solenoid valve, may be disposed along conduit 14 to selectively drain the fluid in lines 45, 18, and 14. A conduit 37 channels fluid from drain 30 in outer vessel 24 to the system 10 drain.

When the reusable second disinfectant is used in system 10, the articles may be prewashed with a detergent. Means 90 for selectively introducing a washing solution into inner vessel 22 may be included in the system 10. Container 84 may include a separate chamber for holding the detergent which may be selectively added to the first disinfectant or may be injected separately through injector 81 into fluid supply line 12 for introduction into inner vessel 22. Alternatively, the detergent may be manually added to inner vessel 22, as in a conventional washing machine. The articles may be washed prior to being placed in the inner vessel. Apparatus 20 would then be used only for disinfecting and sterile rinsing. The following method can be adjusted accordingly.

In operation, articles to be disinfected are placed in the inner vessel 22. The cover 28 is closed and lid 38 of outer vessel 24 is closed. In the preferred method, the articles may be rinsed with tap water to remove any gross residue. Drain 48 is opened during this rinsing phase to immediately remove the gross residue and the initial rinse water from the system 10 through conduits 45 and 14. Valves 86, 72, 76, and 79 are closed. Valves 16 and 77 are open. Alternatively, the articles may be prerinsed before being placed in the inner vessel 22.

The articles are washed in the next phase of the preferred method. Washing may occur by applying any suitable commercially available detergent mixed with water to the articles. The detergent may be added manually or may be injected into the fluid supply for introduction into the inner vessel 22. As stated above, washing may optionally take place before the articles are placed in inner vessel 22. The method would then begin with the rinse and disinfect steps. In the preferred method, however, the washing step takes place in the apparatus 20. Drain 48 is closed while the fluid and detergent are introduced into inner vessel 22. Agitator 58 agitates the fluid-detergent mixture for several minutes to facilitate washing. The time and extent of agitation is dictated by the type of detergent used.

Drain 48 is opened to drain the wash fluid. The articles should then be rinsed to remove any remaining detergent and soil residue.

Drains 48 and 30 are then closed. Any suitable known means for controlling the drains 48 and 30 may be used. A disinfectant is applied, preferably via spray nozzles 56, to the articles in the inner vessel 22 and allowed to overflow into chamber 26 through interface 25 until the inner vessel 22 is submerged in disinfectant. The articles and the inner vessel 22 should soak in the disinfectant for a period of time sufficient to disinfect the articles and the interior and exterior surfaces 21 and 23 of the inner vessel 22, preferably about ten minutes or as dictated by the disinfectant of choice. The agitator 58 may optionally be operated during this period.

If the disinfectant from means 60 is applied, valves 98, 96, 94, and 16 are closed. Valves 92 and 76 are opened. Pump 66 draws the disinfectant from reservoir 64 through conduit 69 through valve 92 into pump 66, and through conduit 67 through valve 76 through line 12 and out of spray nozzles 56. Alternatively, valves 16, 76, 94, and 92 may be closed and valves 98 and 96 may be opened. Pump 66 draws the disinfectant from reservoir 64 through conduit 68 and valve 98 into pump 66 and through conduit 69 and valve 96 into the inner vessel 22 through agitator 58.

If the disinfectant from means 80 is applied, the washing and disinfecting phases of the preferred method are combined. Following the tap water rinse and drain to remove the gross residue, the detergent-disinfectant solution stored in container 84 is metered into the fluid supply line 12 through injector 82 for mixture with the fluid, which is preferably water. Valves 86 and 16 are opened. Valves 72 and 76 are closed. Drains 48 and 30 are closed. The detergent-disinfectant-water mixture is sprayed onto the articles through spray nozzles 56. The mixture fills the inner vessel 22, overflows through interface 25 into chamber 26 to submerge inner vessel 22. The mixture simultaneously washes and disinfects the articles, the interior surface 21 and exterior surface 23 of inner vessel 22 and the interior and exterior of cover 28. Agitator 58 may optionally be operated to facilitate washing. The submersion, or soaking, phase continues for a period of time sufficient to wash and disinfect the articles and the inner vessel 22, approximately ten minutes, or as dictated by the choice of detergent-disinfectant solution.

It is critical that washing either precede or accompany the disinfecting step. Detergents dissolve the protein based soil which can block the way of the disinfectant into irregularities on the surfaces of the articles and the inner vessel 22 in which microbes are lodged. Without first removing the soil by washing, the disinfectant may not reach the microbes.

Following submersion and soaking with either the single-use detergent-disinfectant-fluid mixture or the reusable disinfectant, both drains 48 and 30 are opened to drain the inner and outer vessels 22 and 24. Sterile fluid, preferably sterile water is sprayed onto the articles in inner vessel 22 to rinse any remaining disinfectant. Valves 86 and 16 are closed. Valve 72 has been previously opened to permit the introduction of the water into filters 75. Waterborne microbes and spores are filtered out, yielding sterile water. When it is time to rinse with the sterile water, valve 74 is opened. The sterile water is introduced through spray nozzles 56. In an alternative embodiment of system 10, the tan water may be sterilized by ultraviolet irradiation or by passing the fluid through some suitable known sterilizing agent which can rapidly decompose to a nontoxic substance, such as ozone.

Drain 48 in inner vessel 22 is then closed. The sterile rinse water is allowed to fill inner vesel 22 so that it overflows through interface 25. The sterile rinse water rinses the interior of cover 28. The sterile rinse water flows over the exterior surface of cover 28, rinsing cover 28, and flows down the sides 42, front 43 and back 41 of the exterior surface 21 of inner vessel 22, rinsing those surfaces. Drain 30 remains opened so that there is a steady flow of sterile rinse water over the exterior surface 21 of inner vessel 22. The flows of sterile water through interface 25 from inner vessel 22 over the cover 28 and surface 21 establishes a direction of flow away from the inner vessel 22 which acts as a barrier to the entry of contaminants into inner vessel 22. The flow is maintained for a period of time sufficient to soak the articles in inner vessel 22 and to rinse the exterior surface 21. The sterile water is preferably agitated with agitator 58 during this rinse/soak period to assure complete rinsing of clinically undesirable disinfectant residues.

Drain 48 is then opened to drain the sterile water from inner vessel 22. As a result of the foregoing method of disinfecting and sterile rinsing, the articles in inner vessel 22 and the interior and exterior surfaces 21 and 23 of inner vessel 22 have been disinfected and have been maintained in a disinfected state during and following the rinsing phase. All surfaces facing the articles have been and remain disinfected. When the lid 38 is opened, the cover 28 protects the articles from any contaminated droplets which may fall from the interior surface of lid 38. When cover 28 is opened, all of its surfaces have been disinfected and sterile rinsed so that any droplets remaining on the cover 28 which may fall into the disinfected field of inner vessel 22 will not contain waterborne contaminants. One embodiment of apparatus 20 would provide means (not shown) by which lid 38 and cover 28 could be opened together so that any droplets on the interior of lid 38 would be directed away from the exterior of cover 28. Simultaneous opening of lid 38 and cover 28 would maintain cover 28 as a shield between opening 54 and lid 38 at all times during the opening movement.

Inner vessel 22 may be removable so that the vessel 22 with cover 28 in place could be removed from outer vessel 24 and carried to the area where the disinfected articles are to be used.

Another embodiment of the apparatus 20 of the present invention would provide an outer chamber 24 which would not entirely enclose inner vessel 22 as does the chamber 24 shown in FIG. 1, but would enclose only that portion of inner vessel 22 surrounding cover 28 and interface 25 so that only those enclosed portions are submerged during the disinfect stage and rinsed during the sterile rinsing stage of the process. The areas of critical concern for maintenance of the disinfected field are the interior and exterior surfaces of cover 28, interface 25 and rims 61, 62, and 63 of inner vessel 22 where droplets of contaminated fluid are known to gather in conventional automated equipment and from which such contaminated droplets can drop into the disinfected field when lids are opened and trays bearing the disinfected articles are jostled. The design of cover 28 insures that the sterile fluid and the disinfectant will flow over the interior of cover 28 when the inner vessel 22 fills, through interface 25, contactng rims 61, 62, and 63 and cover edges 51, 52, and 53. The incline of cover 28 along the rise of rims 62 from rim 61 to rim 63 insures the flow over the exterior surface of cover 28.

What is claimed is:

1. A method for disinfecting articles and the exterior and interior surfaces of the vessel in which the articles are disposed in an apparatus for use with a conventional supply of fluid, where the apparatus has an outer vessel and an inner vessel so disposed within the outer vessel that an outer chamber is defined therebetween, the method comprising:

placing the articles in the inner vessel of an apparatus having an inner vessel so disposed within an outer vessel that an outer chamber is defined therebetween;

washing the articles;

draining the inner vessel;

so applying a disinfectant to the articles that the disinfectant fills the inner vessel and flows through an interface between the inner vessel and a cover on the inner vessel to so fill the outer chamber that the inner vessel is submerged for a period of time sufficient to disinfect the articles, the inner vessel and the cover;

draining the inner vessel and the outer chamber;

spraying sterile fluid onto the articles;

so filling the inner vessel with sterile fluid that the articles are substantially submerged and the sterile fluid flows through the interface and over the exterior surface of the cover, establishing a direction of flow for preventing the entrance of contaminants into the inner vessel and rinsing the exterior surfaces of the cover, for a period of time sufficient to soak the articles;

agitating the sterile fluid within the inner vessel; and draining the inner vessel and the outer chamber.

2. A method as recited in claim 1 wherein the sterile fluid is obtained by sterilizing the fluid from the conventional supply by passing the fluid through a plurality of filters adapted for removing bacterial spores from the fluid and delivering the sterilized fluid through a conduit to the inner vessel.

3. A method as recited in claim 1 wherein the disinfectant is obtained by injecting a disinfectant into the supply to fluid and delivering the disinfectant-fluid through a conduit to the inner vessel.

4. A method as recited in claim 1 wherein the inner vessel is filled by closing a drain in the inner vessel, and the outer chamber is filled by closing a drain in each of the outer vessel and the inner vessel, and the inner vessel is drained by opening the drain in the inner vessel and the outer vessel is drained by opening the drain in the outer vessel.

5. A method as recited in claim 1 wherein the steps of washing the articles and applying disinfectant to the articles are combined by injecting a solution of washer-disinfectant into the source of fluid and delivering the washer-disinfectant-fluid mixture to the inner vessel and agitating the washer-disinfectant-fluid mixture for a period of time to wash and disinfect the articles and the inner vessel while the inner vessel is filled with and submerged in the mixture.

* * * * *

UNITED STATES PATENT AND TRADEMARK OFFICE
CERTIFICATE OF CORRECTION

PATENT NO. : 4,617,065

DATED : October 14, 1986

INVENTOR(S) : Craig S. Sundheimer

It is certified that error appears in the above—identified patent and that said Letters Patent is hereby corrected as shown below:

Col. 7, line 8, delete "tan" and substitute therefor --tap--;

Col. 8, line 7, delete "contactng" and substitute therefor --contacting--; and

Col. 8, line 51, delete "to" and substitute therefor --of--.

Signed and Sealed this

Twenty-third Day of December, 1986

Attest:

DONALD J. QUIGG

Attesting Officer

Commissioner of Patents and Trademarks